(12) United States Patent
Piazza et al.

(10) Patent No.: US 8,630,813 B2
(45) Date of Patent: Jan. 14, 2014

(54) METHOD AND DEVICE FOR ASSESSING THE STRUCTURAL CHARACTERISTICS OF INSTALLED SUPPORTING POLES

(75) Inventors: Maurizio Piazza, Isola Vicentina (IT); Gianni Maria Pompermaier, Saonara (IT); Maria Paola Riggio, Cognola (IT)

(73) Assignee: Cinetix S.R.L. (IT)

( * ) Notice: Subject to any disclaimer, the term of this patent is extended or adjusted under 35 U.S.C. 154(b) by 118 days.

(21) Appl. No.: 13/124,915

(22) PCT Filed: Oct. 20, 2009

(86) PCT No.: PCT/IB2009/054608
§ 371 (c)(1),
(2), (4) Date: Apr. 19, 2011

(87) PCT Pub. No.: WO2010/046844
PCT Pub. Date: Apr. 29, 2010

(65) Prior Publication Data
US 2011/0218744 A1    Sep. 8, 2011

(30) Foreign Application Priority Data
Oct. 22, 2008   (IT) .............................. VR2008A0116

(51) Int. Cl.
*G01B 5/28* (2006.01)
(52) U.S. Cl.
USPC .......................................................... 702/35
(58) Field of Classification Search
USPC .............................................. 702/35, 36, 39
See application file for complete search history.

(56) References Cited

U.S. PATENT DOCUMENTS

| 4,702,111 A | 10/1987 | Holland |
| 4,926,691 A * | 5/1990 | Franklin et al. ................. 73/579 |
| 6,711,535 B2 * | 3/2004 | Ford et al. ........................ 704/1 |
| 6,813,948 B1 | 11/2004 | Rinn et al. |

FOREIGN PATENT DOCUMENTS

| EP | 0261487 A2 | 3/1988 |
| EP | 0379622 A1 | 8/1990 |
| WO | WO 2007/052239 A2 | 5/2007 |

OTHER PUBLICATIONS

International Search Report dated May 7, 2010, issued in corresponding international application No. PCT/IB2009/054608.

* cited by examiner

*Primary Examiner* — Stephen Cherry
(74) *Attorney, Agent, or Firm* — Ostrolenk Faber LLP

(57) ABSTRACT

The present disclosure relates to a method for automatically assessing structural characteristics of a supporting pole sunk in the ground, including the operational steps of detecting data regarding a pole being assessed, striking at least one blow against said pole, detecting pole oscillations generated by said struck blow(s), analyzing detected oscillations in order to determine at least one significant parameter of the oscillation trend, and comparing said significant parameter(s) with pre-established threshold values in order to obtain a conformity or non-conformity index related to pole characteristics.

19 Claims, 9 Drawing Sheets

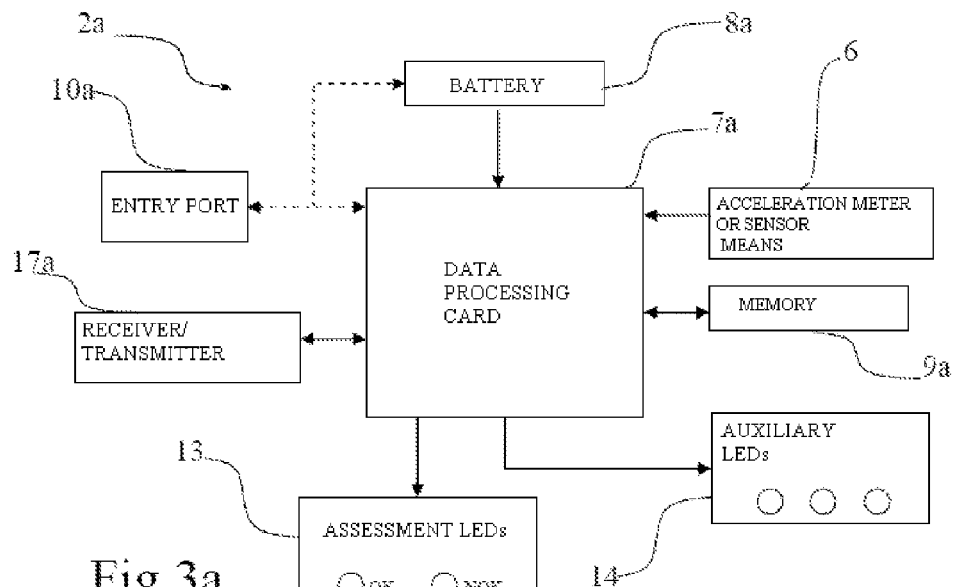
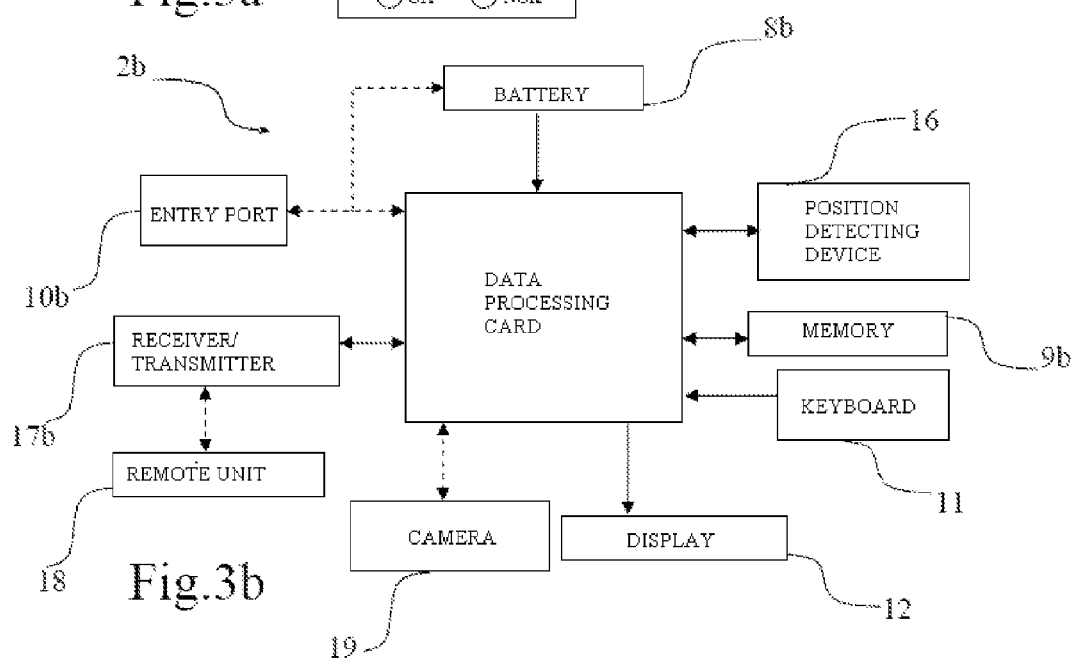

METHOD AND DEVICE FOR ASSESSING THE STRUCTURAL CHARACTERISTICS OF INSTALLED SUPPORTING POLES

CROSS REFERENCE TO RELATED APPLICATIONS

The present application is a 35 U.S.C. §371 National Phase conversion of PCT/IB2009/054608, filed Oct. 20, 2009, which claims benefit of Italian Application No. VR2008A000116, filed Oct. 22, 2008, the disclosure of which is incorporated herein by reference. The PCT International Application was published in the English language.

BACKGROUND OF THE INVENTION

The present invention concerns a device and a method for assessing the structural characteristics of supporting poles installed or sunk in the ground, particularly supporting poles made of wood, reinforced concrete, fiberglass and the like.

In many rural areas, links with telephone and/or electrical networks (lines) are of the "overhead" type, i.e. telephone and/or electrical cables are carried on top of substantially vertical and sunk in the ground supporting poles. Said supporting poles are, usually slightly tapered upwards, present generally circular in cross-section and are typically made of wood.

It is often necessary to carry out maintenance work along a line. Such maintenance work can be planned over time or can be required occasionally, e.g. after an unexpected failure of the electrical and/or telephone cables supported by poles. Line maintenance work requires the intervention of operators who, by using ladders or crampons, climb to the top of the supporting poles to carry out the required operations.

Supporting poles are originally sunk deeply in the ground and must maintain over time structural characteristics sufficient to allow an operator to climb up to the top of a pole safely, without risking pole being broken or overturned, e.g. when its portion sunk in the ground is not sufficiently firm. Fatal accidents due to a supporting pole in a line being broken during maintenance work are unfortunately anything but uncommon.

In order to avoid serious accidents to operators and faults in line cables, periodic inspection of the structural conditions of poles is required. Should poles not meet pre-determined technical requirements, they must be replaced.

In the present description and in the claims, the term "constraint conditions" of a supporting pole is used to describe a set of forces exerted on the pole, in order to keep it in an substantially vertical position, also on steep and impervious ground. Constraint conditions, therefore, include both the action exerted on the pole by the terrain in which it is sunk (the so called ground-level constraint), and forces applied to the pole by any auxiliary supporting pole and/or by tension wires suitably applied to it (the so called ground anchoring system).

In the present description and in the claims, the term "material degradation" of a supporting pole is to be understood to mean degradation of mechanical characteristic features of the material of which the pole is made of, typically wood, i.e. modulus of elasticity, mechanical resistance and volume mass, and possibly reduction in cross-section of the supporting pole actually capable of withstanding stresses caused, for example, by an operator climbing to the top of the pole.

The term "structural degradation" of a supporting pole means, instead, any modification in the static conditions of the pole with respect to its initial installation, e.g. due to modifications in constraint conditions, and more particularly modifications in the ground-level constraint or in the geometric characteristics of the installed supporting pole, especially those modifications which result in a reduction of the pole resisting cross-section.

That being said, factors which can compromise the reliability of installed wooden poles, e.g. in telephone lines, are essentially two: "material degradation", i.e. the degradation of the wood forming the pole, and "structural degradation" of the pole.

"Material degradation" of a wooden pole occurs with a progressive decay of the wood, e.g. due to attack by fungi. Such a decay is generally limited to the underground portion of a supporting pole and can also affect supporting poles perfectly integral and sound above-ground.

In so far as the "structural degradation" is concerned, modifications in the constraint conditions or in the initial geometric conditions can occur, for instance, owing to incorrect installation of the supporting pole, or damage to the ground anchoring system (e.g., breaking of an auxiliary supporting pole), collapse of the ground in which the pole is sunk, or organic degradation of the underground portion of the pole.

All the above mentioned degradation factors can obviously impair the safety of a supporting pole. Thus, it is essential to assess the risk an operator, who is going to climb to the top of a supporting pole to carry out maintenance work, is running. Such an assessment should be in "closed form", i.e. it should make it possible to spot the existence of risk for the operator and the gravity of such risk, independently of the cause or the specific type of degradation of the pole being assessed.

There are currently available several (manual or automated) methods for assessing the structural characteristics of a supporting pole.

Manual methods of assessment have long been disclosed, which require shaking a supporting pole being tested in a direction perpendicular to both the longitudinal axis of the pole and the direction in which the cables supported by it extend, in order to ascertain whether the pole is suitably sunk in the ground. is The pole is, then, struck with a hammer and to the sound emitted by the poles listened to: a dull and hollow sound indicates a poor state of the pole structure. Then, by digging the soil at the base of the pole to a depth of about 30 cm, i.e. in the area where pole can more easily decay, the state of preservation of the wood is visually ascertained.

Other methods involve, instead, the use of automatic devices. The method developed by the Swiss Federal Institute of Technology in Lausanne provides for the of e.g. a device, termed POLUX that by means of two suitably shaped electrodes which are inserted into the supporting pole being assessed at ground level measures the force of penetration exerted by the device while the two electrodes are inserted and the degree of humidity of the pole wood. The force of penetration is correlated with wood density, and thus with the resistance of the supporting pole to bending stress applied to the pole, e.g. by the operator while climbing the pole, whereas the degree of humidity is correlated with the extent of biological decay of wood fibers.

According to another well-known method, a device, commercially known under the name of RESISTOGRAPH® (distributed by RINNTECH of Heidelberg, Germany), is employed which is suitable for recording the wood resistance to penetration of a suitably shaped drill bit, said drill bit rotating and advancing in the wood at a constant speed. The wood resistance to the drill bit penetration is correlated with structural characteristics of the pole.

Another known method requires the use of a device termed POLESCAN (manufactured by IAMSL Ltd., New Zealand), which makes it possible to test a pole by means of ultrasound probes positioned at the base of the supporting pole being assessed.

Such manual procedures have the disadvantage of being subjective, since assessment of pole characteristics depends on subjective evaluation by the operator. Bearing in mind that in order to carry out maintenance operations of a line an operator has to climb the poles, understandably enough often he is willing to be strict in his assessment, and as a consequence about 20% of the poles classified as "to be replaced" are still in good condition, i.e. having structural characteristics meeting pre-established technical requirements of a high degree of safety.

In so far as the methods employing the above mentioned automatic devices are concerned, they have the disadvantage of relying on measurements which, although objective, regard exclusively the assessment of the wood conditions, and do not consider the integrity of the geometric characteristics or the ground-level constraint of the pole.

In addition, as these methods are based only on local examinations, they measure the structural properties of a wooden pole only at a pole point or area where these measurements are made, and thus they are not representative of the whole structure of the supporting pole.

Another drawback of automatic methods is that they use relatively large devices, too heavy and cumbersome for an operator who has to move along the line, between one pole and the next, for example in wooded or cultivated country.

Another drawback of the methods known in the art is that they do not provide any evidence of an executed test. In case of fault along a line or an accident to the operator, it is, indeed, desirable and advantageous for the company responsible for the maintenance along that line to be able to prove that the assessment and planned maintenance of the poles in the line was carried out in an accurate and punctual way.

Not the last drawback of known methods, both manual ones and those involving the use of devices such as RESISTOGRAPH® and POLUX, is that they are invasive, with the risk of compromising the structural characteristics of a pole being measured, as they require, e.g. removal of a sample of pole material, or drilling holes in the supporting pole.

SUMMARY OF THE INVENTION

Thus, the main object of the present invention is to provide a method and a device for non-invasive assessment of the structural characteristics of a supporting pole.

Another object of the present invention is to provide a method and a device for objective assessment of structural characteristics of a supporting pole.

Another object of the present invention is to provide a method and a device for detecting structural characteristics of a supporting pole, in which global characteristics of the pole under assessment, i.e., those regarding its entire structure, are measured, not only those concerning the area around a small portion of the supporting pole where the measurement is made.

Still another object of the present invention is to provide a method and a device for the assessment of a supporting pole which produces an evidence of the executed assessment/measurement of the structural characteristics of the pole.

A further object of the present invention is that of providing a method of assessment of a supporting pole which makes it possible the use of a light detecting device small in size.

Another object of the present invention is to provide a method of assessment of a supporting pole designed to optimize the time schedule of maintenance operations on supporting poles in a line.

A further object of the present invention is that of providing a method of assessing the structural characteristics of a supporting pole which is simple and easy to carry out.

A last object of the present invention is to provide a device for assessing structural characteristics of a supporting pole which can be manufactured at competitive costs.

According to a first aspect of the present invention, there is provided a method of automatically assessing the structural characteristics of a supporting pole sunk in the ground, comprising the following steps:
 detecting data concerning a pole being assessed;
 applying at least one blow to the pole;
 detecting pole oscillations generated by the blow(s);
 analyzing detected oscillations to determine at least one parameter representative of the oscillation trend; and
 comparing the parameter(s) thus obtained with pre-established threshold values to obtain an index of conformity or non-conformity, of the characteristics of the pole.

According to another aspect of the present invention there is provided a device for carrying out the method of automatically assessing structural characteristics of a supporting pole sunk into the ground, according to any claim from 1 to 29, comprising a supporting structure provided with anchoring members designed to maintain, in use, said supporting structure in contact with the surface of said pole at a height from the ground, and at least one programmable control unit supported by said supporting structure, and including:
 at least one sensor means designed to detect pole oscillations in response to at least one blow struck to the pole and to generate at least one electrical signal correlated with the trend of the measured oscillations;
 at least one data processing card designed for processing said at least one electrical signal in order to determine at least one parameter correlated with the trend of measured oscillations and to generate at least one output signal; and
 at least one indicator means which acts in response to said at least one output signal.

Further features and advantages of the present invention will appear more clearly in the following description of two currently preferred embodiments, given exclusively for non-limiting and illustrative purposes, with reference to the attached drawings, in which:

BRIEF DESCRIPTION OF THE DRAWINGS

FIGS. 3a and 3b illustrate block diagrams of two programmable control units (the main one in FIG. 3a and an auxiliary one in FIG. 3b), which belong to the device of the present invention according to a second embodiment of the invention;

DESCRIPTION OF PREFERRED EMBODIMENTS

Figure 1:
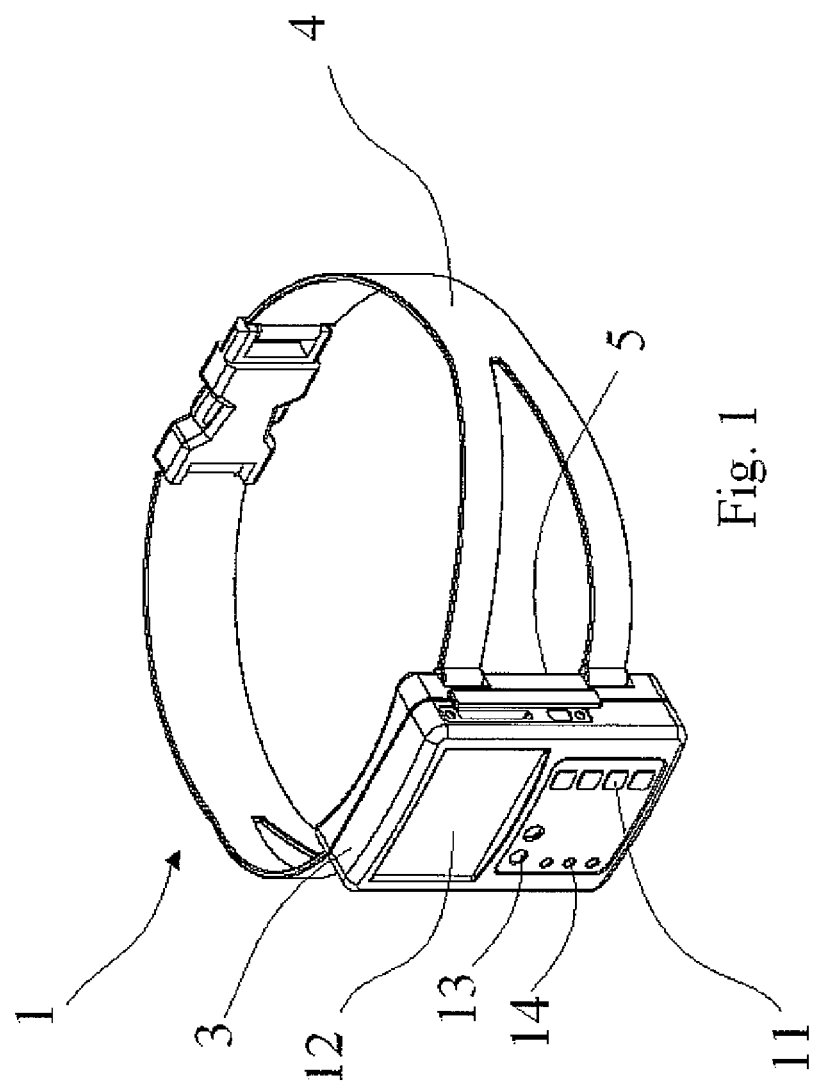
FIG. 1 shows a perspective view slightly from above, of a device according to the present invention.

In the accompanying drawings, parts or components identical or similar have been assigned the same reference numerals.

Figure 2:
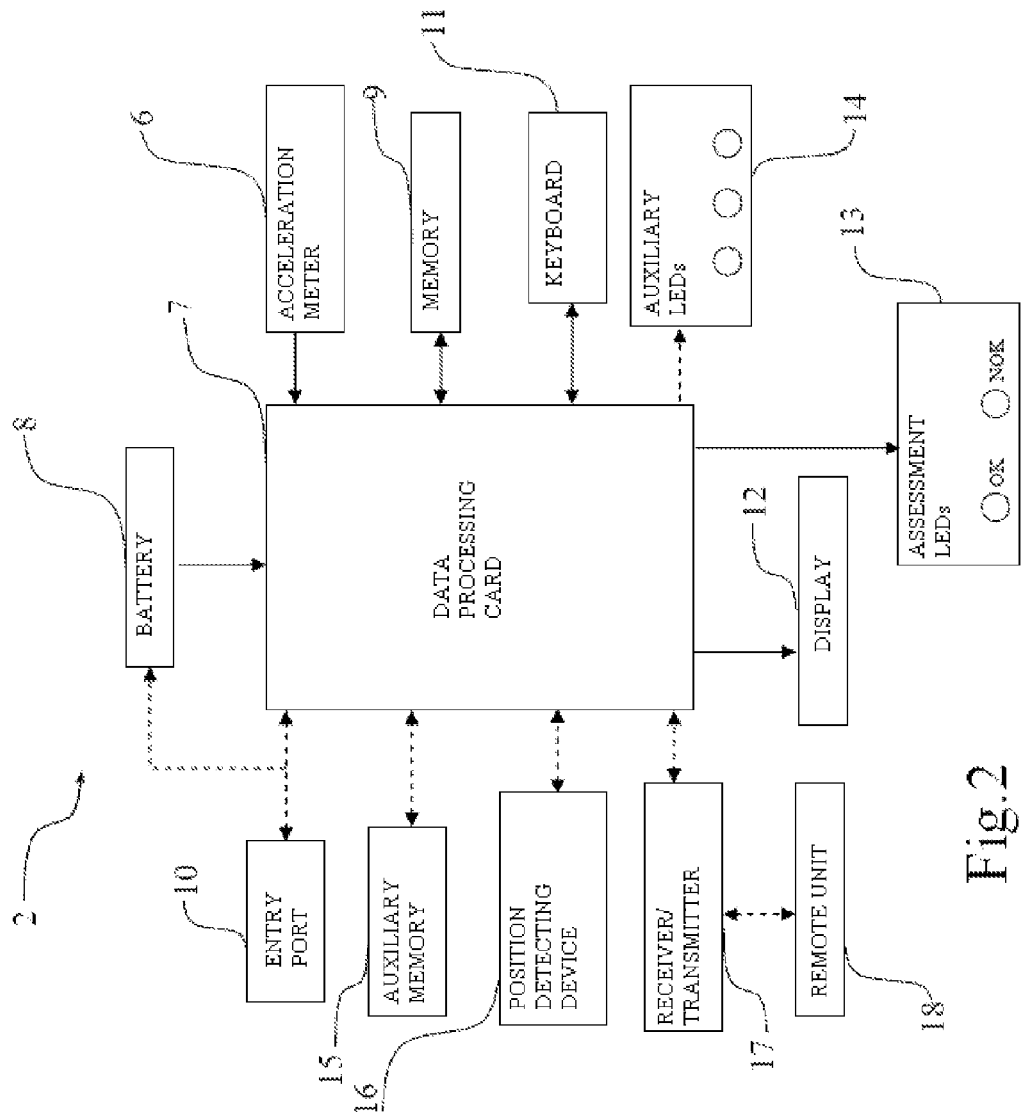
FIG. 2 illustrates a block diagram showing the components of the device of FIG. 1, according to a first embodiment of the invention.

Referring first to FIGS. 1 and 2, it will be noted that a device for assessing a supporting pole P is generally indicated by 1 and comprises a programmable control unit 2, housed in a supporting structure 3, which structure is advantageously shaped as a housing box.

The housing box or case 3 is provided with anchoring mechanisms, e.g. elastic belts 4 which, in use, are designed to encircle a supporting pole P being tested at a height H from the ground. The housing box 3 typically has one of its outer faces 5 which, in use, remains in contact with the supporting pole P. The programmable control unit 2 in the housing box 3 has at face 5 a sensor means, preferably an acceleration meter or accelerometer 6, suitable for generating an electrical signal s(t) in response to accelerations of pole P caused by a mechanical stress (one or more blows) given to the external surface of the pole, e.g. a blow struck with a hammer or mallet by an operator.

The acceleration meter or sensor means 6 is electrically connected to a data processing card (7), which can be powered, e.g. by rechargeable batteries 8 of Li-Io type. The data processing card 7 is designed to receive the electrical signal s(t) measured by sensor means 6 and send it to a memory 9, where it is stored. The electrical signal s(t) can be then (pre) processed by the data processing card 7 and (pre)processing results can be stored in memory 9.

Advantageously, in the programmable control unit 2 there is provided an entry port 10, e.g. a USB port, electrically connected to both data processing card 7 and battery 8. Said entry port 10 is designed to preferably establish an electrical connection between battery 8 and an external electrical network, in order to recharge the battery. In addition, entry port 10 electrically connects memory 9 to programmable control unit 2, e.g., by an outer data processing unit (not shown in the drawings), in which signal s(t), previously stored in memory 9, can be transferred and further processed.

Data processing card 7, which is designed to control (by sending suitable electric signals) all the components of programmable control unit 2, to which it is electrically connected, also comprises access means, e.g., a keyboard 11 and a displaying means (e.g., a display 12), through which an operator can enter (and thus memorize) and view, respectively, data (e.g., in alphanumerical format) regarding a supporting pole P being tested. These data are typically: the height of the pole (usually indicated on a plaque secured to the surface of the supporting pole with other specific geometric characteristics of the pole), diameter of the pole cross-section, as measured at height H, and further optional information, such as presence of visible cracks in the pole, provision of any auxiliary pole as a support for pole P being assessed, the identification code of the operator testing the pole, data and time of assessment, etc.

The programmable control unit 2 also includes two indicator means, e.g., using LEDs, designed to show a certain number of conditions of the unit itself. More particularly, a first indicator means comprises so called "assessment LEDs" 13, which generate a signal light in response to processing of a signal s(t) acquired by sensor means 6, such processing being carried out by the data processing card 7 to indicate whether the supporting pole P being assessed complies with technical specifications (LED OK shows green light), or not (LED NOK shows red light).

The second indicator means, or "auxiliary" group 14, comprises LEDs which light up at certain operating conditions, such as the turning on of the device, the establishment of a link to an external data processing unit through entry port 10, low level of battery 8, etc.

With particular reference to FIG. 2, it will be noted that an auxiliary memory 15, such as an ordinary SD card, is optionally provided in the programmable control unit 2, the memory 15 being designed to store large quantities of data regarding, for example, any pole assessment carried out by an operator over a certain time interval (one month, one year, etc.).

It will be noted that an auxiliary memory 15 of this type has the advantage of being easily removable from the processing control unit 2, and thus a great quantity of data stored therein can be further processed even after assessment of a specific pole P, example. g., by an external data processing unit or computer (not shown in drawings), obviously equipped with a suitable reader for the auxiliary memory 15.

Thus, starting from data stored in memory 15, graphs can be advantageously developed, various kinds of statistical studies can be carried out, and detailed analyses can be made.

Optionally, programmable control unit 2 also includes a position detecting device 16, e. G. a GPS which, when activated, is designed to detect absolute coordinates of the device 1, and thus of the supporting pole P to which device 1 is applied, with a negligible margin of error for this type of applications. Advantageously, geographical coordinates measured by device 16 can be stored in memory 9 of the programmable control unit 2 together with data of the supporting pole P being assessed, the date and time of the assessment (as already indicated above), the identification code of the operator who has carried out the assessment, etc. Any such data can, advantageously, provide proper evidence of both the presence at the site of a given operator and the executed assessment of a pole P. As mentioned above, after an accident, the maintenance company could be bound to provide evidence of the assessment/maintenance work carried out on a supporting pole P along a certain line. With this type of device, such evidence can be produced very rapidly and fully free of errors.

The programmable control unit 2 is also advantageously equipped with a receiver/transmitter 17, e.g. one employing radio waves, designed to exchange in real time if so desired with a remote unit 1, e.g., a centralized remote data processing unit located even at great distance, any data concerning operator's assessments, including date and time of the assessment of a pole P, the electrical signal s(t) recorded by sensor means 6, additional data (presence of cracks in the pole, etc.), assessment results (OK, or NOK), data on the operator who carried out the pole assessment, and so on.

The advantages of being in a position of transmitting, and thus carrying out group processing of data concerning poles P of one or more lines, are as numerous as obvious. These advantages include the possibility of obtaining, in an obvious manner for the skilled person, a prediction index regarding complying with safety specifications of a pole so that it will be possible to optimize planning of pole assessment in a line, e.g. by postponing assessment of poles expected to comply with the required safety specifications for at least a few years, and to plan instead more frequent checks on supporting poles which, although already checked and found to be "satisfactory", barely meet safety standards.

With reference to FIGS. 3a and 3b, it will be noted that device 1 of the present invention can comprise, according to a second embodiment of the present invention, two programmable control units: a main one, shown in FIG. 3a, and an auxiliary one illustrated in FIG. 3b.

According to this second embodiment, the housing box 3 of device 1 as applied, in use, to a pole P being assessed at a height H from the ground preferably includes the main programmable control unit 2a.

Similarly to programmable control unit 2 of FIG. 2, the main programmable control unit 2a comprises a data processing card 7a, e.g. powered by battery 8a, and designed to control (by sending control signals and receiving/processing response signals) any device electrically connected to it, i.e., an acceleration meter or sensor means 6, a memory 9a, two indicator or signaling means 13 and 14 (e.g., LEDs), and one receiver/transmitter 17a.

According to this second embodiment, the data processing card 7a is designed only to pre-process electrical output signal s(t) from the acceleration meter 6. Such pre-processing is e.g. designed to reduce background noise and reckoning, in a obvious manner for the skilled person, computational parameters to be used for subsequent processing of signal s(t). Other functions of these components are the same as those briefly described with reference to FIG. 2.

With reference, instead, to FIG. 3b, it will be noted that the auxiliary programmable control unit 2b, such as a hand-held computer, comprises a data processing card 7b, also powered by a battery 8b, and is designed not only to control any device electrically connected to it, but also and especially to process signals/data from the receive/transmitter 7b.

The card 7b is also designed to process data which are stored in memory 9b and were entered by the operator through access keyboard 11 or were acquired automatically by devices electrically connected to card 7b, e.g. the position detecting device 16, already described with reference to FIG. 2.

More particularly, according to this second embodiment, the receiving/transmitting device 17a of the main programmable control unit 2a is designed to send, example. g. through radio waves or infrared radiation, the electrical signal s(t) detected by sensor means 6, or in any case its pre-processed version, to the auxiliary programmable control unit 2b. Signal s(t) is received by the receiver/transmitter 17b of the auxiliary programmable control unit 2b and processed by the data processing card 7b together with other data stored in memory 9b.

Besides the position detecting device 16, the programmable control unit 2b optionally comprises a digital camera 19, e.g. of the type commonly incorporated in cell-phones, the camera being used by an operator to photograph the pole to be assessed.

Data processing card 7b is designed to perform also the analysis of the photograph/digital image acquired by camera 19. More particularly, by processing the digital photograph taken by the operator, it is possible to automatically retrieve both the diameter of the cross-section of pole P at height H at which device 1 is applied, and the entire height of pole P to be evaluated, as well as other data, such as the degree of tilt of the photographed pole P with respect to the ground, etc.

The receiving/transmitting device 17b is also advantageously designed to send the results of the processing of signal s(t) (carried out by card 7b) to receiver/transmitter 17a of the main programmable control unit 2a. Such results, together with other data stored in memory 9b, can also be optionally transmitted to a remote unit 18, as illustrated in FIG. 2.

The auxiliary programmable control unit 2b also comprises a displayer 12, like that illustrated in FIG. 2, designed to visualize any data regarding the assessment of a pole P.

Lastly, both programmable control units 2a and 2b advantageously comprise entry ports 10a and 10b, as those described with reference to FIG. 2.

The operation of a device 1 for assessing a supporting pole, according to the above described first embodiment, is very simple and reliable, and illustrated in flow diagrams of FIGS. 4a, 5a, 6a and 7a.

Figure 4A:
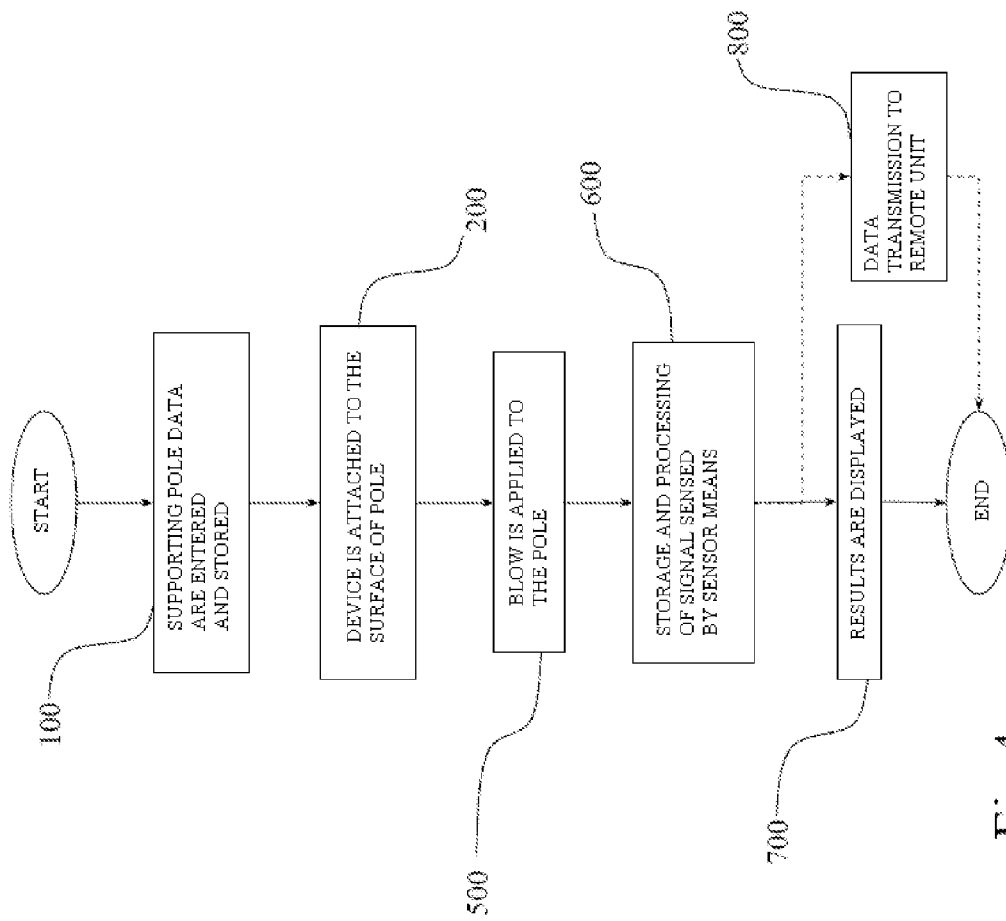
FIGS. 4a and 4b show a flow diagram of the main steps of the method according to two different embodiments of the present invention.

FIG. 4a shows the main steps of the method of pole assessment according to the present invention. More particularly, the initial step of the method (step 100) comprises data entry and storage of data on the supporting pole P being assessed in the programmable control unit 2.

Subsequently, at step 200, the device 1 is suitably attached to the supporting pole P (in a convenient manner by means of elastic belts 4) at a height H from the ground. It will be noted that the order in which steps 100 and 200 are carried out is unimportant, i.e., step 200 (attachment of device 1 to the surface of the supporting pole P being assessed) can be carried out before the data entry step 100, without altering the result of the method according to the present invention.

In the next step, step 500, a blow is applied to the pole which is thus caused to oscillate around its vertical axis, the oscillations gradually decreasing until they disappear after some time.

Oscillation of pole P or, rather, the variation in time of the oscillation speed (acceleration) of the pole P, is measured by sensor means 6 in step 600, and is translated into an electrical signal s(t) which is processed by the data processing card 7 that, in response to said processing, generates at least one output signal. The output signal from data processing card 7 is then sent to displayer 12 and to LED indicator group 13. In response to such signal, the displayer 12 displays a suitable message (step 700), thus informing the operator whether the pole P meets pre-established safety requirements (technical specifications), whereas the indicator group 13 generates a signal light by lightening one of the LEDs (green light: OK; red light, NOK). It was experimentally found that the modes of oscillation of a pole are correlated both to its structural characteristics and to the solidity of its ground-level constraint, and can thus conveniently represent a global objective (not concerning a mere point or zone) parameter for the assessment thereof.

Together with step 700 (display of results), any data concerning the pole P assessment can optionally be sent through receiver/transmitter 17 to a remote unit 18 where, as already described above, they are stored and possibly further processed.

The main steps of the above described method are described in greater detail down below.

Figure 5A:
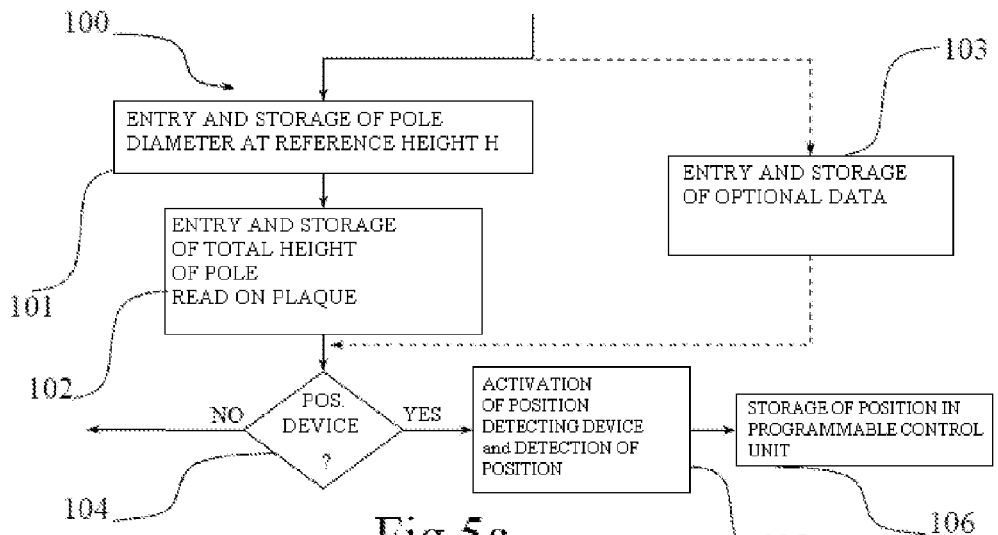
FIGS. 5a and 5b illustrates two flow diagrams concerning data entry and storage according to two different embodiments of the present invention.

Details of step 100 on data entry regarding the supporting pole are shown in the flow diagram of FIG. 5a. In a first step 101, the operator manually measures, example. g. with a flexible measuring tape, the diameter of the supporting pole at a given reference height H from the ground, at which device 1 is then attached. Such measurement result is entered in the programmable control unit 2 through keyboard 11 and stored in memory 9. In step 102, besides the diameter value of pole P, the operator also enters and stores in memory 9 the total height of pole P being assessed, that can be read on a plaque secured to the pole. In step 103, by means of keyboard 11, the operator can optionally store in memory 9 other optional data (see above)—example. g., his identification code, date and time of assessment, indications on visible cracks in the pole, existence of any auxiliary poles for the supporting pole, etc.

Subsequently, should the device 1 be equipped with a position detecting device (step 104), the operator will activate such a detector (step 105) and, in step 106, absolute coordinates of the position of device 1 (approximately coinciding with those of pole P being assessed) are stored in memory 9 of the programmable control unit 2.

At this point, step 200, the operator applies device 1 to an area on the surface of pole P at height H. In this step, the device is preferably applied to the surface of the pole, in such a manner that face 5 of device 1 designed to be in contact with pole P is located along the orthogonal projection on the pole of the overhead cables supported by the pole. In so far as the height H with respect to ground level, at which device 1 is applied, is concerned, such height will be chosen by the operator in such a way that the application of device 1 is comfortable and does not require the use of ladders or the like. It will be easily understood that such height H will range approximately between 1 and 2 meters.

The operator may advantageously be provided with a stiff measuring stick A, of pre-determined length, e.g., 1.5 meters, so that device 1 can always be applied by the operator at the same height H with respect to the ground, i.e., the length of the measuring stick A.

The use of the measuring stick A has two advantages: firstly, the method becomes "standardized", i.e., it does not depend on the operator subjectivity, so that assessment results are more easily comparable with one another; secondly, the depth to which supporting pole P is sunk into the ground can be ascertained. The plaque bearing the structural characteristics of pole P is, in fact, always applied by the pole producer at the same height with respect to the bottom end of the pole itself. Thus, as the height at which the plaque is applied is known, and the distance between its point of attachment and height H at which device 1 is applied is also known, the depth to which pole P extends underground can be estimated.

Once the device 1 has been applied to the surface of a supporting pole P, the operator strikes a blow to the pole (step 500), e.g. with a mallet. The blow is struck approximately at the level of device 1 and at an angle substantially perpendicular to both the direction of the overhead cables carried by the supporting pole P and its longitudinal axis. Thus, the consequent oscillation of pole P with respect to its vertical axis is less damped in time and, therefore, more easily detectable by sensor means 6. Obviously, the blow has to be struck with a minimum of sufficient force in order to generate an oscillation correctly detectable by sensor means 6. The skilled person will easily understand that data processing card 7, once signal s(t) is stored in memory 9, will check the amplitude of that signal s(t) and, if necessary, will generate an error message should the signal not be of sufficient amplitude to be correctly processed, and step 500 must be repeated.

Figure 6A:
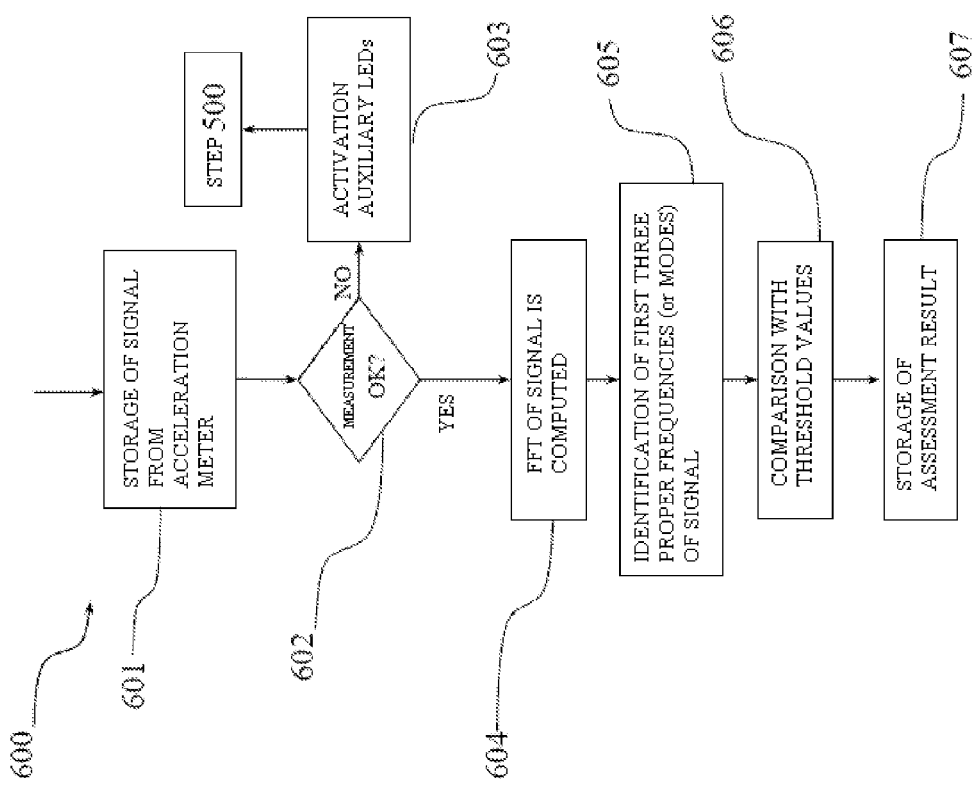
FIGS. 6a and 6b show two flow diagrams on the storage and processing of a signal measured by an acceleration meter according to two different embodiments of the present invention.
Figure 6B:
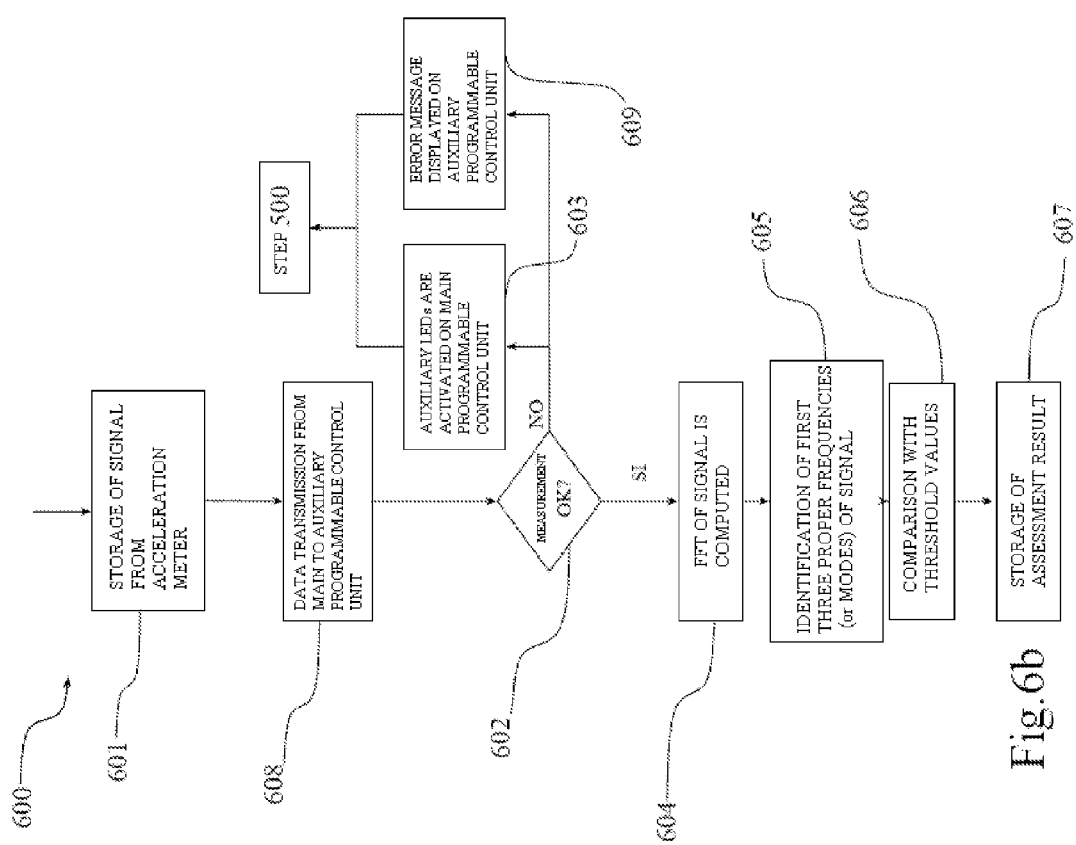
Figure 7A:
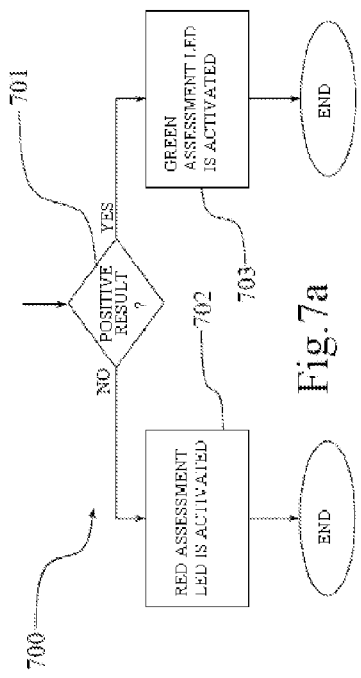
FIGS. 7a and 7b show two flow diagrams on data presentation, according to two different embodiments of the present invention.
Figure 7B:
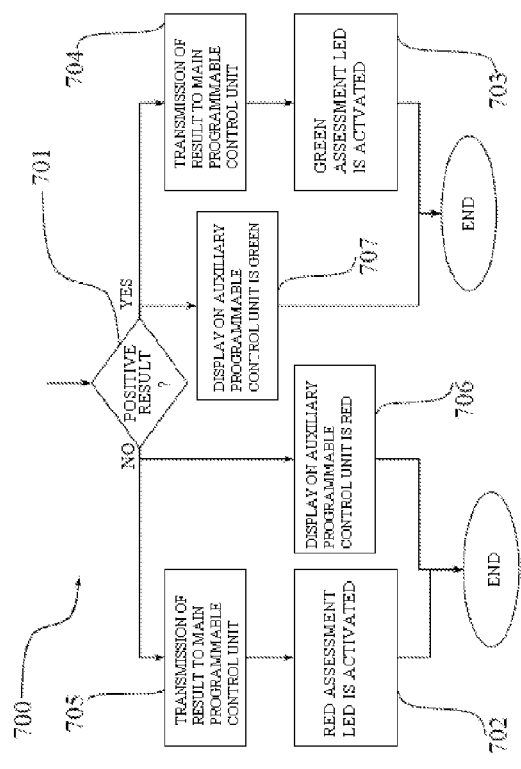

In so far as step 600 on storage and processing of signal s(t) detected by sensor means 6 is concerned, this step is illustrated in the flow diagram of FIG. 6a. Signal s(t) is stored in memory 9 in step 601 and, if the measurement was not carried out properly (step 602), LED indicator group 14 is activated (step 603) in a suitable manner. After that, the system returns to step 500.

If signal s(t) has been correctly acquired, in step 604 data processing card 7 processes the Fast Fourier Transform (FFT) of signal s(t), which is thus converted into the frequency domain. In step 605, values of the first three modes or frequencies ($f_1$, $f_2$ and $f_3$) of the frequency domain signal (referred to as S(f)) are identified.

The pole is assessed by comparing, at step 606, frequency values $f_2$ and $f_3$ and frequency ratio $f_2/f_3$ with suitable threshold values. Oscillation frequencies of a supporting pole P are correlated, as mentioned above, to the structure of the material of which the pole is made and the solidity of its ground-level constraint.

A supporting pole P is considered to comply with the requirements if all three compared values ($f_2$, $f_3$, $f_2/f_3$) are higher than threshold values.

As to the threshold values, frequency intervals outside which a pole is classified as "not complying with standards" have been determined by computerized simulation studies of stresses a wooden supporting pole P undergoes while an operator climbs up to the pole top. The intervals determined by the simulation (threshold values±tolerances) have been subsequently validated by laboratory experiments designed to assess the resistance to bending stress of 20 wooden supporting poles and to obtain a model linking the modulus of elasticity of a pole to its breaking point, starting from: the diameter of the pole P at the height H of application of the device 1, the overall pole height, and the oscillation frequencies of the pole after being struck. Half of these 20 poles 10 was previously classified by a maintenance operator as "in good condition" and the other half was classified as in need of being replaced.

The threshold values were then refined by more than 100 "field" assessments on supporting poles P, and by comparing the results obtained by applying the method and a device according to the present invention with the results the manual assessment by an operator.

Threshold values as determined above are specific for the material the poles are made of (in the specific case, pine or chestnut wood), and also depend on specific geometric characteristics of the poles and degree of rigidity of the constraints which the poles are subjected to.

In any case, threshold values for supporting poles made of materials other than wood, e.g., concrete, can be determined in the same way.

Going back to the method implemented by device 1, after comparison at step 606, at step 607 the results are stored in the memory 9 and data processing card 7 sends an output signal to indicator means 13 which generates a signal light (step 701, FIG. 7a) according to the received signal.

More particularly, if the supporting pole P complies with technical standards, the green LED lights up (step 702); otherwise the red LED lights up (step 703).

Optionally, a suitable message for the operator can be displayed on display 12 every time an indicator (13 or 14) is activated. This option is not shown in the drawings.

The operation of the device according to the second embodiment of the present invention is now described, mainly highlighting the differences with respect to the operation of the above disclosed first embodiment. Such an operation is illustrated in flow diagrams in FIGS. 4b, 5b, 6b, and 7b.

Figure 4B:
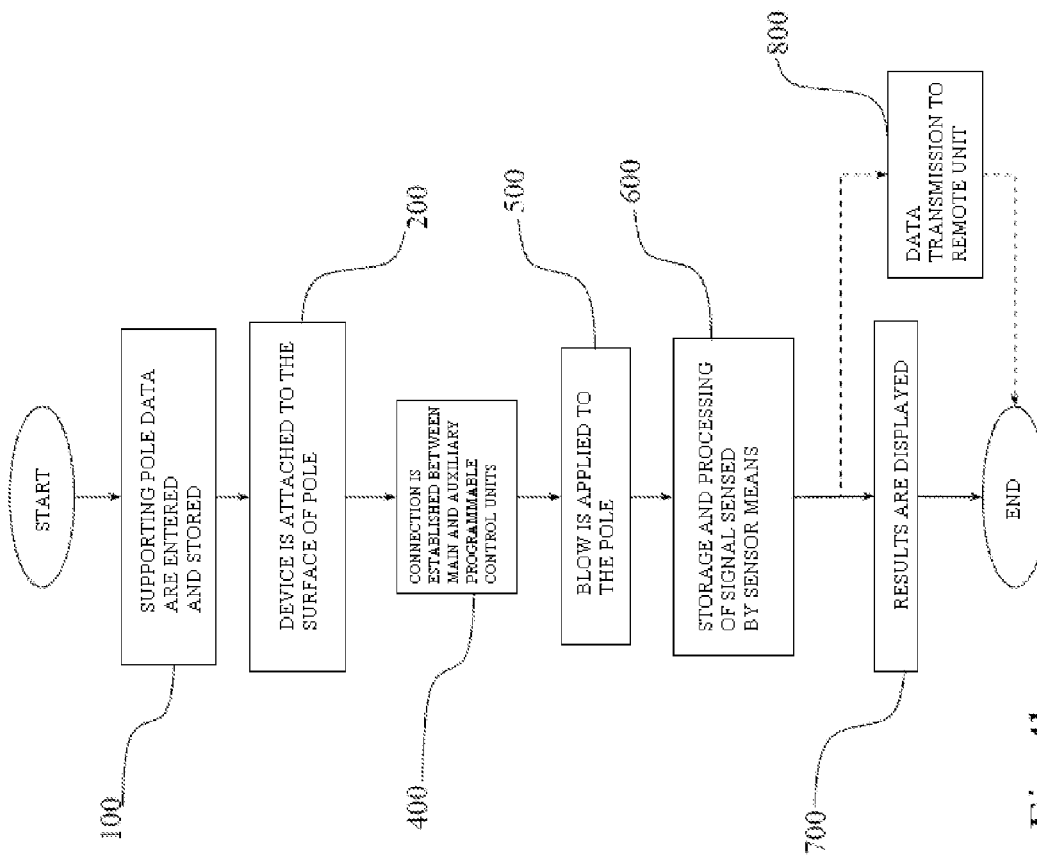

Likewise FIG. 4a, FIG. 4b illustrates the main operation steps of the operation of the device according to the present invention. At steps 100 and 200, supporting pole data are entered and stored, and the device 1 is attached to the surface of a pole P being assessed. As already mentioned with reference to the first embodiment, the order of execution of these two steps is irrelevant—in theory, such steps can also be carried out at the same time if, for example, the assessment of the pole is carried out by two operators. One operator can apply the device to the supporting pole being assessed and, in the meantime, the other can enter pole data to the auxiliary programmable control unit 2a by means of keyboard 11.

Once these two steps are completed, at step 400 connection by radio or infrared radiation is established between the main programmable control unit 2a and the auxiliary programmable control unit 2b. A skilled person in the art will understand how establishing of the connection between programmable control units 2a and 2b can be signaled to the operator(s) by generating a suitable control signal from data processing cards 7a and 7b. In response to such a signal, e.g., the LEDS of indicator group 14 on main programmable control unit 2a will light up and an appropriate message is visualized on the display means of the auxiliary control unit 2b.

Step 400 is followed by a step 500 concerning the application of a blow to the pole, a step 600 dealing with storing and processing of the signal detected by the accelerometer on the main programmable control unit 2a, and a final step 700 where the results are displayed. Step 700 is optionally executed at the same time as step 800, step 800 concerning the transmission of said results and data stored in memories 9a and 9b to a remote data processing unit 18.

Figure 5B:
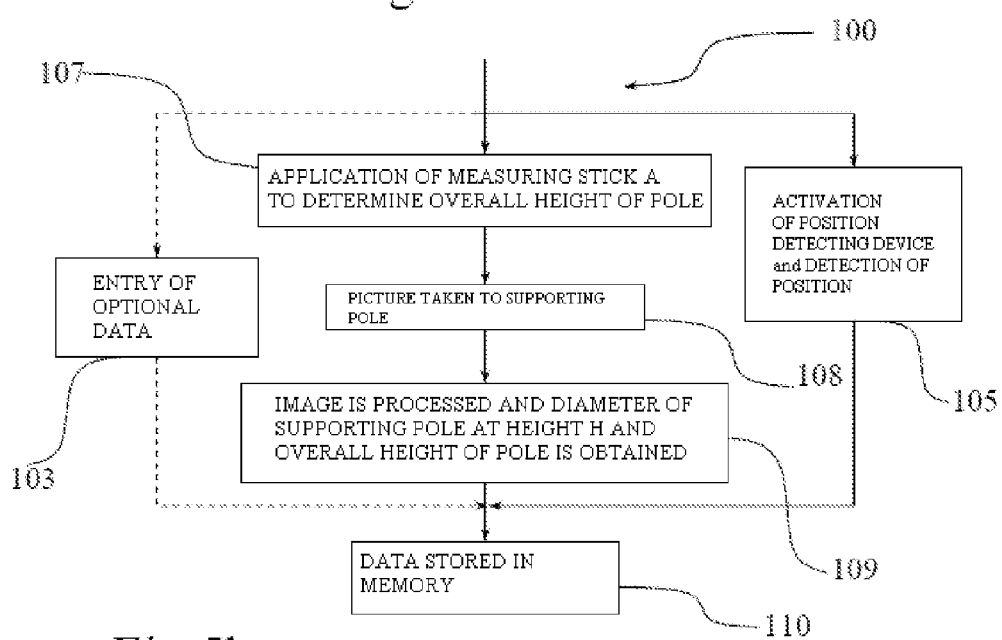

In more detail, at step 100 shown in FIG. 5b the operation of entering data concerning a pole P is partly manual and partly automated. More particularly, at step 105, the position detecting device is energized (by sending a suitable control signal), and automatically acquires the absolute coordinates of the auxiliary programmable control unit 2b. The operator, either in the mean time or subsequently, can lean the measuring stick A (described above) against the supporting pole P (step 107), in such a manner that one end of measuring stick A is in contact with the ground. The operator then takes a digital photograph with camera 19 of the auxiliary programmable control unit 2b. At step 109, the image acquired and stored in memory 9b is processed and the diameter of the supporting pole P at the upper end of measuring stick A and the overall height of pole P being assessed is obtained.

Optionally, the operator can load optional pole data unit 2b through keyboard 11, as above pointed out.

Once all these operations have been completed, at step 110 all the acquired data are stored in memory 9b.

At step 100, or either immediately before or immediately after, the device 1 is applied to the surface of the pole P (step 200) at the upper end of the measuring stick A and preferably, as noted above, in the direction of the orthogonal projection on the pole of the overhead cables carried by the pole. During step 400, a connection is established between programmable control units 2a and 2b by means of respective receiver/transmitters 17a and 17b which exchange suitable identification signals in any suitable manner, as it is well-known for a skilled person. After identification between the two units, the receiver/transmitter 17a enters a "transmission" mode and the receiver/transmitter 17b enters a "reception" mode.

At this point, at step 500, the operator strikes a blow against the supporting pole P being assessed, as already described in connection with the first embodiment.

In so far as step 600 concerning storage and processing of electric signal s(t) detected by accelerometer 6 in the main programmable control unit 2a, this signal is stored in memory 9a and pre-processed by data processing card 7a. Card 7a generates a suitable output signal (that codifies therein also the signal s(t) detected by the accelerometer 6) which is transmitted (step 608) to the receiver/transmitter 17a, and from receiver/transmitter 17a is forwarded to receiver/transmitter 17b in the auxiliary programmable control unit 2b, where it is stored in memory 9b, while awaiting for being further processed.

Data processing card 7b also checks, in any suitable way easily understandable by a skilled person, the quality of the signal acquired by the accelerometer 6 (step 602). If the signal is not acquired correctly, at steps 603 and 609, the data processing card 7b sends appropriate output signals both to the display 12 on the auxiliary unit 2b, which visualizes a suitable error message, and to the receiver/transmitter 17b (now in "transmission" mode), which sends such output signal to the receiver/transmitter 17a (in "reception" mode) of the main programmable control unit 2a, where the LEDs of the indicator means 14 are thus suitably lightened.

If instead the signal has been acquired correctly, at steps 604, 605, and 606, data processing card 7b computes the FFT of the signal, identifies the first three modes, or proper frequencies ($f_1$, $f_2$ and $f_3$) of the signal, and compares the values of $f_2$, $f_3$ and $f_2/f_3$ with the threshold values determined as described above. The result of this comparison is then stored in memory 9b.

In so far as visualization of results (step 700) is concerned, the data processing card 7b codifies such results in a suitable output signal and sends such signal (steps 704 and 705) via receiver/transmitter 17b and 17a also to the main programmable control unit 2a where, in response to such signal, suitable LEDs of the indicator means 13 light up (steps 702 and 703). In the auxiliary programmable control unit 2b, instead, the output signal generated by data processing card 7b is sent to the display 12 which, in response, turns green (step 703), if the result of the assessment is positive (pole P complies with standards), or red (step 706) if it is negative (pole P does not comply with standards).

The device and the method of pole assessing as described above may be subjected to many modifications and variations within the scope as defined in the claims.

Thus, for instance, the device 1 according to the second embodiment can comprise one programmable control unit 2a including all the components of programmable control unit 2 according to the first embodiment.

Moreover, device 1 can comprise a hammer, whose handle has its free end mounted for rotation on a hinge pin secured to the belt anchoring mechanisms 4 at an angular distance of about 90° with respect to the housing box 3. Once the device 1 has been attached to the pole by means of its elastic belts 4, the hinged end of the hammer handle in removably armed with any suitable type of arming means easily available to a skilled person, in a "waiting" position by means of suitable locking means (e.g., a hammer linkage). In such "waiting" position, the mallet is positioned with its handle substantially parallel to the longitudinal axis of the supporting pole fully above the elastic belts 4.

At step 500, once the hammer lever has been activated and thus unlocked, the mallet experience an angular excursion, e.g. due to gravity only, of about 180° between its upper waiting position and its lower working or striking position, where the mallet is located completely below the elastic belts 4.

It will be noted that, in a configuration of this type, the striking step 500 of the pole being assessed is advantageously standardized.

What is claimed is:

1. A method of non-invasively and automatically assessing global structural characteristics of a supporting pole sunk in the ground, the method comprising the following operational steps:

acquiring data on the supporting pole being assessed, the acquiring comprising establishing an overall height and diameter of a cross-section of the pole, the diameter being measured at a pre-established height of the pole above ground;

striking at least one blow against said pole to generate pole oscillations;

detecting the pole oscillations generated by said at least one blow;

analyzing detected pole oscillations to determine at least one significant parameter in an oscillation trend; and comparing said at least one significant parameter with pre-established threshold values to obtain a conformity-non-conformity index related to pole characteristics, wherein said at least one significant parameter is a modulus of elasticity of said pole and said threshold values are calculated based on a model linking said modulus of elasticity to a breaking point of said pole, starting from said overall height of said pole.

2. A method according to claim 1, wherein said overall height and diameter of said cross-section of said supporting pole is obtained by processing of an image acquired by a digital camera.

3. A method according to claim 1, wherein said acquiring step is performed by at least one position detecting device and comprises the steps of:

activating the position detecting device and establishing the position thereof; and storing said position in a memory.

4. A method according to claim 1, wherein said acquiring step includes detecting optional data comprising an identification code of an operator assessing the pole, and the date and time of assessment of the pole.

5. A method according to claim 1, wherein said pre-established threshold values are correlated with a stiffness degree of constraints to which said pole is subjected.

6. A method according to claim 5, wherein said constraints for said pole comprise a ground anchoring system.

7. A method according to claim 1, wherein said striking of at least one blow to said pole takes place in a direction orthogonal to both the longitudinal axis of the pole and the overhead cables carried at the top of said pole.

8. A method according to claim 1, wherein said striking of at least one blow to said pole takes place approximately at a pre-established height from ground.

9. A method according to claim 1, wherein the method further comprises:

at least the application to said pole of at least one device for measuring pole oscillations generated by the at least one blow struck thereagainst, and said application of said at least one device occurs in an area of the surface of the pole along one direction substantially corresponding to the orthogonal projection on the pole of the overhead cables at the top of the pole and at a pre-established height from ground.

10. A method according to claim 1, wherein said pre-established height is approximately 1.5 meters.

11. A method according to claim 1, wherein said step of detecting pole oscillations generated by said at least one blow comprises transmitting said detected data and said detected oscillations to at least one auxiliary programmable control unit.

12. A method according to claim 11, wherein said conformity-non-conformity index is obtained through at least one further processing by said auxiliary programmable control unit.

13. A device implementing the method of automatic assessing structural characteristics of a supporting pole sunk in the ground according to claim 1, the device comprising a support structure equipped with anchoring members designed, in use, to keep said support structure in contact with the surface of said pole at a height from ground, and at least one programmable control unit supported by said support structure and including:

at least one sensor configured to measure pole oscillations in response to the at least one blow struck against the pole and to generate at least one electrical signal correlated with the trend of detected oscillations;

at least one data processing card configured to process said at least one electric signal to determine at least one parameter correlated with the detected oscillation trend and to generate at least one output signal; and at least one indicator configured to be energized in response to said at least one output signal.

14. A device according to claim 13, wherein said at least one programmable control unit comprises:

at least one position detecting device configured to detect the position coordinates thereof, and at least one memory for storing said position.

15. A device according to claim 14, wherein said at least one position detecting device comprises a GPS.

16. A device according to claim 14, wherein the device comprises at least one auxiliary programmable control unit comprising at least one digital camera.

17. A device according to claim 16, wherein the device comprises at least one position detecting device.

18. A device according to claim 14, wherein the device comprises a striker configured to strike the at least one said pole.

19. A device according to claim 18, wherein said striker comprises:

a mallet having its free end pivoted on a hinge pin secured to said anchoring members at an angular distance of about 90° with respect to the support structure and configured to rotate through about 180° between an upper waiting position, where said mallet is completely above said anchoring members, and a lower working position, where said mallet is fully below said anchoring members.

* * * * *